US010859486B2

(12) United States Patent
Boverman et al.

(10) Patent No.: US 10,859,486 B2
(45) Date of Patent: Dec. 8, 2020

(54) SYSTEMS AND METHOD FOR DOWN-HOLE PHASE MONITORING

(71) Applicant: General Electric Company, Schenectady, NY (US)

(72) Inventors: Gregory Boverman, Saratoga Springs, NY (US); Sachin Narahari Dekate, Guilderland, NY (US); Yongjae Lee, Latham, NY (US)

(73) Assignee: GENERAL ELECTRIC CO., Schenectady, NY (US)

( * ) Notice: Subject to any disclaimer, the term of this patent is extended or adjusted under 35 U.S.C. 154(b) by 612 days.

(21) Appl. No.: 15/607,181

(22) Filed: May 26, 2017

(65) Prior Publication Data

US 2018/0340879 A1    Nov. 29, 2018

(51) Int. Cl.
| | | |
|---|---|---|
| *G01N 15/10* | (2006.01) | |
| *G01N 15/14* | (2006.01) | |
| *G01V 3/26* | (2006.01) | |
| *G01V 3/30* | (2006.01) | |
| *G01N 27/02* | (2006.01) | |
| *E21B 49/08* | (2006.01) | |
| *G01V 1/50* | (2006.01) | |
| *G01N 33/28* | (2006.01) | |

(52) U.S. Cl.
CPC ....... *G01N 15/1031* (2013.01); *E21B 49/088* (2013.01); *G01N 15/14* (2013.01); *G01N 27/026* (2013.01); *G01V 1/50* (2013.01); *G01V 3/26* (2013.01); *G01V 3/30* (2013.01); *E21B 49/0875* (2020.05); *G01N 27/025* (2013.01); *G01N 33/2823* (2013.01)

(58) Field of Classification Search
CPC .................................................. G01N 15/1031
USPC ............................................................. 702/6
See application file for complete search history.

(56) References Cited

U.S. PATENT DOCUMENTS

| 3,778,706 | A | 12/1973 | Thompson |
| 5,453,693 | A | 9/1995 | Sinclair et al. |
| 6,023,445 | A | 2/2000 | Cook et al. |
| 2001/0050559 | A1 | 12/2001 | Wisler et al. |
| 2005/0274513 | A1 | 12/2005 | Schultz et al. |
| 2008/0030415 | A1 | 2/2008 | Homan et al. |

(Continued)

FOREIGN PATENT DOCUMENTS

WO    2012/052764 A1    4/2012

OTHER PUBLICATIONS

International Search Report and Written Opinion issued in connection with corresponding PCT Application No. PCT/US2018/032897 dated Aug. 29, 2018.

(Continued)

*Primary Examiner* — Ricky Ngon

(57) ABSTRACT

A measurement tool configured to be run through a bore of a hydrocarbon well. The measurement tool includes a dielectric core, a controller disposed at a first end of the dielectric core, a first wire helically disposed about the dielectric core and extending from the controller to a first location a first distance from the controller, and a second wire helically disposed about the dielectric core and extending from the controller to a second location a second distance from the controller. The controller provides first and second input signals to the first and second wires, and receives first and second reflected signals from the first and second wires.

19 Claims, 9 Drawing Sheets

(56) References Cited

U.S. PATENT DOCUMENTS

| | | | |
|---|---|---|---|
| 2013/0241561 A1* | 9/2013 | Allen | G01V 3/28 |
| | | | 324/338 |
| 2013/0261977 A1* | 10/2013 | Shanks | G01V 3/30 |
| | | | 702/11 |
| 2014/0239959 A1* | 8/2014 | Clarkson | G01V 3/10 |
| | | | 324/338 |
| 2014/0253128 A1* | 9/2014 | Shanks | E21B 47/102 |
| | | | 324/324 |
| 2015/0337622 A1* | 11/2015 | Lopez | E21B 43/12 |
| | | | 166/66.6 |
| 2016/0033468 A1* | 2/2016 | Shanks | G01N 33/2823 |
| | | | 324/324 |
| 2016/0041286 A1 | 2/2016 | Sinha et al. | |
| 2016/0248143 A1 | 8/2016 | Hensarling et al. | |

OTHER PUBLICATIONS

Tan, Chao, et al.; "Oil-water two-phase flow measurement with a V-cone meter in a horizontal pipe", Instrumentation and Measurement Technology Conference, Singapore, 2009, I2MTC 09, IEEE, pp. 62-67, May 5-7, 2009.

Wu, Dongyue, et al.; "Notice of Retraction Measurement of oil content in oil-water two-phase flow using Coriolis flow meter", Computer Application and System Modeling (ICCASM), 2010 International Conference on, Taiyuan, pp. V5-336-V5-339, Oct. 22-24, 2010.

* cited by examiner

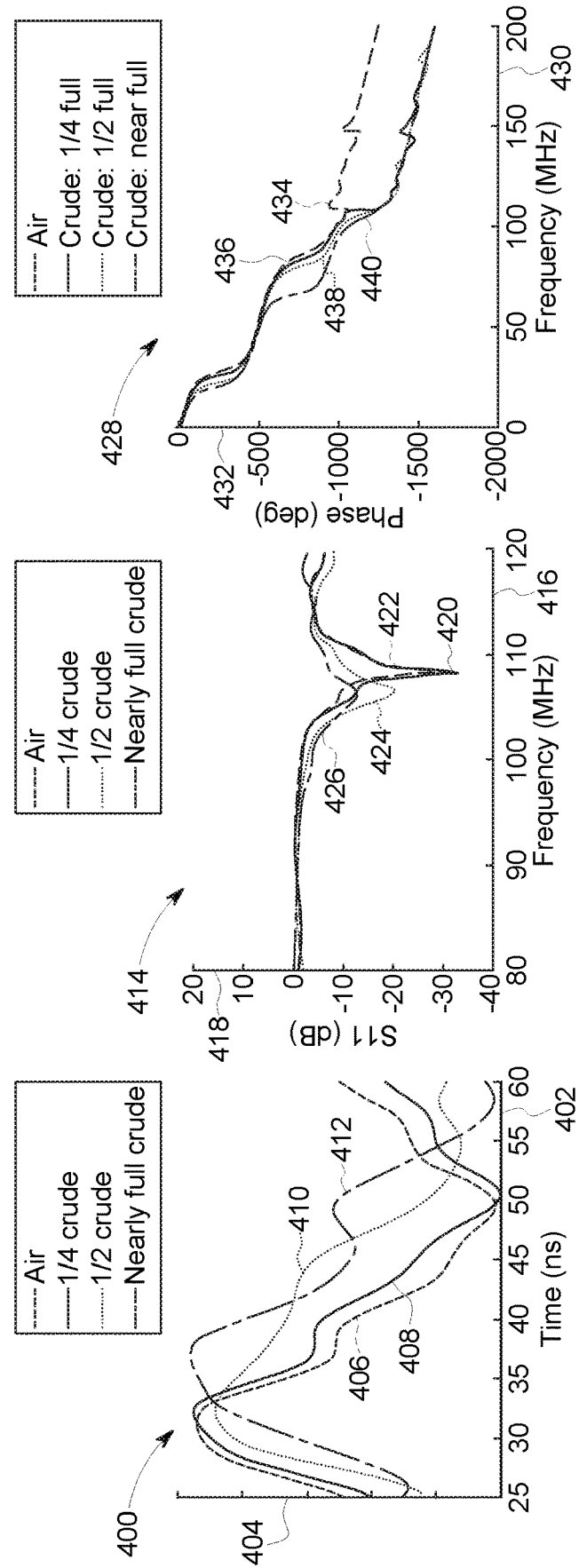

SYSTEMS AND METHOD FOR DOWN-HOLE PHASE MONITORING

BACKGROUND

The subject matter disclosed herein relates to fluid phase monitoring, and more specifically to fluid phase monitoring as fluid flows through a bore.

Subterranean hydrocarbon deposits may be accessed by drilling a bore that extends from the surface of the earth to the hydrocarbon deposit, and then pumping hydrocarbons up to the surface through the bore. Chemicals may be injected into the bore at one or more locations along the bore to improve the flow rate of hydrocarbons through the bore. However, if the composition (e.g., ratio of crude oil to water) of a fluid flowing through the bore is not known at or near the various injection points, an operator may make decisions regarding chemical injection that do not improve the quantity of hydrocarbons produced by the well.

BRIEF DESCRIPTION

Certain embodiments commensurate in scope with the original claims are summarized below. These embodiments are not intended to limit the scope of the claims, but rather these embodiments are intended only to provide a brief summary of possible forms of the claimed subject matter. Indeed, the claims may encompass a variety of forms that may be similar to or different from the embodiments set forth below.

In one embodiment, a measurement tool is configured to be run through a bore of a hydrocarbon well. The measurement tool includes a dielectric core, a controller disposed at a first end of the dielectric core, a first wire helically disposed about the dielectric core and extending from the controller to a first location a first distance from the controller, and a second wire helically disposed about the dielectric core and extending from the controller to a second location a second distance from the controller. The controller provides first and second input signals to the first and second wires, and receives first and second reflected signals from the first and second wires.

In a second embodiment, a system includes a measurement tool configured to be run through a bore of a hydrocarbon well and a computing device. The measurement tool includes a dielectric core, a controller disposed at a first end of the dielectric core, a first wire helically disposed about the dielectric core and extending from the controller to a first location a first distance from the controller, and a second wire helically disposed about the dielectric core and extending from the controller to a second location a second distance from the controller. The controller provides the first and second input signals to the first and second wires, and receives the first and second reflected signals from the first and second wires. The computing device is configured to analyze the received first and second reflected signals to determine a first dielectric constant of a fluid in the bore at the first location, and a second dielectric constant of the fluid in the bore at the second location.

In a third embodiment, a method includes running a measurement tool down a bore of a hydrocarbon well, wherein, the measurement tool comprises a first wire disposed about a dielectric core and extending from a controller to a first location a first distance from the controller, and a second wire disposed about the dielectric core and extending from the controller to a second location a second distance from the controller, wherein the first wire and the second wire are disposed about the dielectric core in a helical shape, providing, via the controller, first and second input signals to the first and second wires, and receiving, via the controller, first and second reflected signals from the first and second wires.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 11 is a plot of a time domain response to an input waveform for a pipeline filled with air, a ¼ crude oil mixed fluid, a ½ crude oil mixed fluid, and a full crude oil fluid, in accordance with an embodiment;

FIG. 12 is a plot of a frequency domain amplitude response to an input waveform for the pipeline filled with air, the ¼ crude oil mixed fluid, the ½ crude oil mixed fluid, and the full crude oil fluid, in accordance with an embodiment;

FIG. 13 is a plot of a frequency domain phase angle response to an input waveform for the pipeline filled with air, the ¼ crude oil mixed fluid, the ½ crude oil mixed fluid, and the full crude oil fluid, in accordance with an embodiment.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The disclosed techniques include systems and methods for determining the composition of static or flowing fluid in a bore of a hydrocarbon extraction system at multiple locations. Specifically, one or more wires are wrapped around a dielectric core in a helical shape. The one or more wires may be of different lengths, extending to various locations along the measurement tool. Excitation signals (e.g., single pulses or more complex input waveforms spanning a range of frequencies) are emitted to the wires and propagate down the lengths of the wires, reaching the ends of the wires, and then propagating back along the wires. The reflected waves or frequency responses are received and analyzed to determine a delay in each signal propagating down the wires. Based on the analysis, the dielectric constant of the fluid flowing through the bore may be determined at each of the locations. If the dielectric constants of each component fluid (e.g., water, crude oil, etc.) are known, then the composition of the fluid may be determined. Using this information, decisions regarding what chemicals to inject, where, and how much, may be made to improve the production of hydrocarbons by the well.

Figure 1:
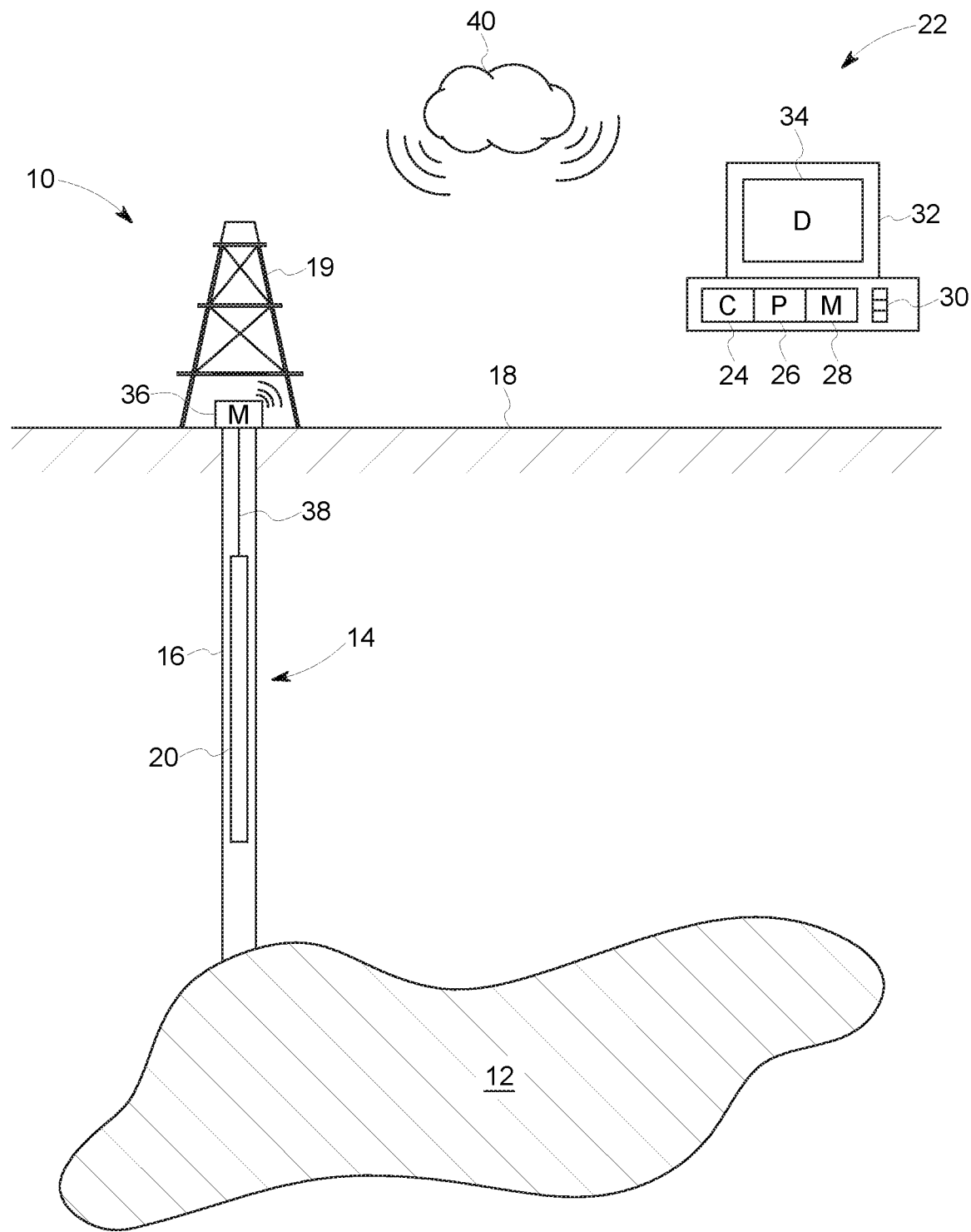
FIG. 1 is a schematic of an embodiment of a hydrocarbon extraction system and a measurement tool, in accordance with an embodiment.

FIG. 1 is a schematic of an embodiment of a hydrocarbon extraction system 10. Oil and/or gas may be accessed from subterranean hydrocarbon deposits 12 via a well 14. For example, a bore 16 may extend from the surface 18 to the hydrocarbon deposit 12. Though the bore 16 shown in FIG. 1 extends vertically from a drilling rig 19 at the surface 18 to the hydrocarbon deposit 12, the bore 16 may extend at an angle oblique to the surface 18. Similarly, the bore 16 may change directions as it extends from the surface 18 to the hydrocarbon deposit 12. That is, the bore 16 may include portions that extend oblique to, perpendicular to, or parallel to the surface 18. Fluid from the hydrocarbon deposit 12 may be extracted (e.g., pumped to the surface 18) via the bore 16. A measurement tool 20 may be inserted into the bore 16 to monitor the phase composition of the fluid flowing past it through the bore 16. As will be discussed in more detail below, the measurement tool 20 emits electromagnetic signals and then measures the reflected waves, or the frequency response. Based on the delay in the reflected waves or the response, the capacitance of the composite fluid flowing through the well 14 can be determined. If the dielectric constants of the various component fluids flowing through the well 14 are known, the makeup of the composite fluid may be determined or estimated.

Data collected using the measurement tool 20 may be analyzed using an external computing device 22 (e.g., computer, tablet, mobile device, etc.), or a combination thereof. The computing device 22 may include communication circuitry 24, a processor 26, memory 28, communication ports 30, and a user interface 32, which may include a display 34. While the measurement tool 20 collects data, or following data collection by the measurement tool 20, data may be passed to a memory component 36 (e.g., via cable 38), which may be located at the surface 18, or within the measurement tool 20, for storage until the data is processed. In other embodiments, collected data may be passed to the computer 22 wirelessly (e.g., via the cloud 40) or through a wired connection via communication ports 30. The computer 22 may be located near the drilling rig 19 or remote from the well 14. In some embodiments (e.g., the computer 22 is located remotely relative to the well 14), the data may be passed to the computer 22 via the cloud 40 or over a network. In other embodiments, the computer 22 may be in wireless communication with the measurement tool 20 while the measurement tool 20 collects data within the bore 16 and analyzing data in real time or near real time. The computer 22 may be outfitted with software stored on the memory component 28 and executed by the processor 26 to facilitate analysis of the collected data. For example, the computing device 22 may be capable of post-processing the data collected by the measurement tool 20, and determining the phase components of fluid flowing through the bore 16 at discrete locations.

Figure 2:
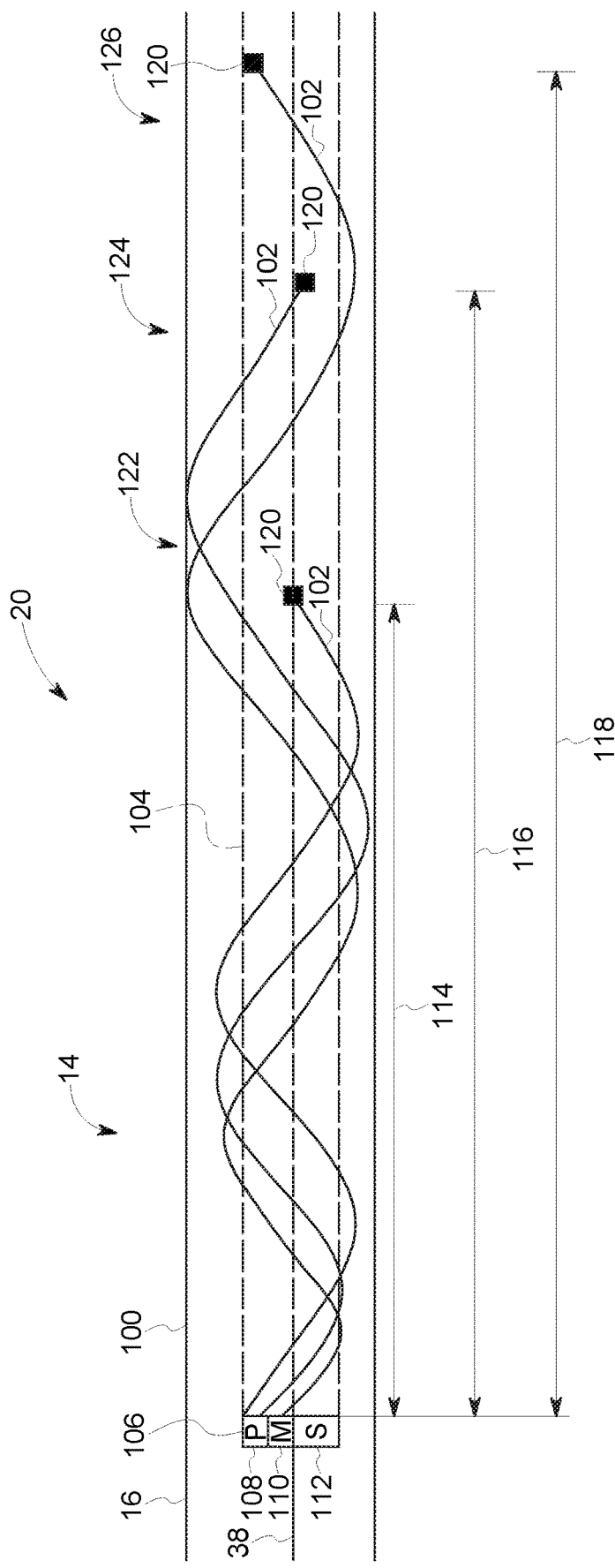
FIG. 2 is a schematic view of the measurement tool of FIG. 1, in accordance with an embodiment.

FIG. 2 is a schematic view of the measurement tool 20 shown in FIG. 1. As shown, the bore 16 is defined by a pipeline wall 100. The measurement tool 20 includes a plurality of wires 102 wrapped (e.g., in a helical fashion) around a dielectric core 104 (e.g., cable). In general, wires 102 wound in a helix have more sensitivity than wires extending axially along the core 104, but are not so tightly wound that the wires 102 have a substantial inductance. In some embodiments, the wires 102 may have a coating (e.g., PTFE coating). The wires 102 may be coupled to a controller 106, which may emit signals into the wires 102 and measure reflections of the emitted signals or frequency response. As shown, the controller 106 may include a processor 108, a memory device 110, and one or more sensors 112. In other embodiments, the controller 106 may be more passive, emitting signals sent from the surface 18 via the cable 18 and passing measurements collected up to the memory device 36 at the surface 18 via the cable 38.

Though three wires 102 are shown in FIG. 2, it should be understood that the embodiment shown in FIG. 2 is merely one possible embodiment and that embodiments with different numbers of wires 102 are also envisaged. For example, the measurement device 20 may include 1, 2, 4, 5, 6, 7, 8, 9, 10, 11, 12, 13, 14, 15, 16, 17, 18, 19, 20, or more wires 102. The wires have different lengths, such that the wires 102 wrap around the core 104 and extend various lengths 114, 116, 118 down the core 104. In some embodiments, each wire 102 may include a mechanism 120 that opens and closes a circuit between the respective wire 102 and the pipeline wall 100. The mechanism 120 may be a servo or a different kind motor (e.g., linear motor) that brings the wire 102 into contact with the pipeline wall 100, a switch, or some other mechanism. In some embodiments, the wires 102 may be shorted against one another. The end point of each wire is referred to as a marker.

The controller 106 emits electromagnetic signals into the wires 102, which propagate through the wires. Measurements and analysis may be time domain focused, frequency domain focused, or both. For example, the emitted signals may be short time domain pulses. The reflected waves may then be measured, as in time domain reflectometry. Additionally, or in the alternative, the emitted signals may include long excitations (e.g., sinusoidal excitations or some other pattern generated using Fourier transforms) over a wide range of frequencies. The frequency response (e.g., amplitude and phase) to the excitations may then be measured. In some embodiments, a vector network analyzer (VNA) may be used. Frequency domain measurements may take several seconds, while time domain measurements may only take several hundred nanoseconds. In some embodiments, multiple time domain measurements may be averaged to improve signal quality. Because the system (i.e., the wires 102, the pipeline wall 100, and the fluid flowing through the pipeline) is linear (i.e., passive), there should be equivalence between time-domain and frequency-domain. Wires 102 may be probed individually, all at once, or in various combinations. The one or more sensors 112 measure reflected signals or frequency response to the emitted signals. From the electromagnetic signatures, a delay experienced by the signals traversing the wires 102 may be determined. The delays may be caused by the different speeds at which the signals propagate through fluids with different dielectric constants. For example, the dielectric constant of water is about 80, while the dielectric constant of oil is 3. Differences in dialectic constants cause signals to propagate through the different fluids at different speeds, resulting in different propagation times, and thus, different time and frequency delays. Based on the determined delay, an estimate of the dielectric constant of the composite fluid may be determined. If the dielectric constants of the various component fluids are known, then the makeup of the composite fluid may be determined.

In effect, the measurement tool 20 measures capacitance between the wires 102 and the pipeline wall 100, wherein pipeline wall is used as a ground or reference plane. As will be described in more detail below, signal processing techniques may be used to determine the composition (e.g., percentage of oil, water, air, natural gas, etc.) of the fluid flowing through the bore 16 at various locations 122, 124, 126, which generally correspond to the various locations of the marker of each respective wire 102. For example, in the illustrated embodiment, the first location 122 is a first distance 114 from the controller 106, the second location 124 is a second distance 116 from the controller 106, and the third location 126 is a third distance 118 from the controller 106.

A frequency response approach to measurement and analysis may provide more thorough information regarding the fluid flowing through the pipeline, but using frequency response can be complicated. For example, in some instances, it may be difficult to distinguish signals from one another. In some embodiments, difference imaging (e.g., measuring responses in two different wires and subtracting the resultant time domain signals) may be used to determine the location of an end of a wire 102. Further, using the same excitation signal (i.e., input signal) using multiple wires, or multiple combinations of multiple wires, in both open and short conditions, may help to generate a more complete picture of the fluid flowing through the pipeline wall 100. For example, sending the same excitation signal through multiple wires of different lengths 102 and comparing the responses makes it relatively easy to determine where the markers are. Further, opening and closing the circuit may help to determine propagation delays and the location of the end of tool. The propagation delays may then be used to determine the effective dielectric properties of the fluid at each location. If the dielectric properties of the various component fluid are known, the makeup of the fluid at each location may be determined.

Figure 3:
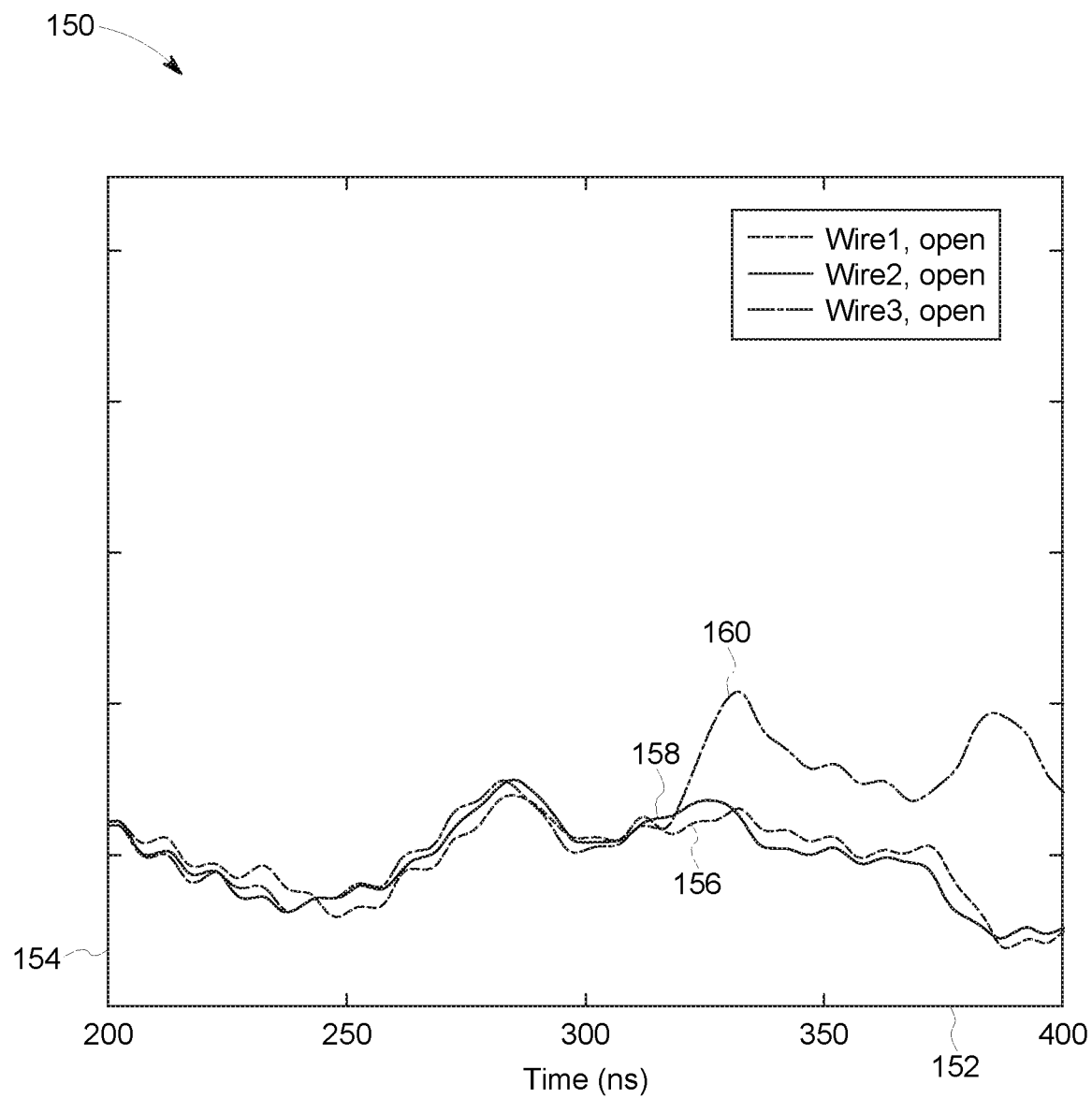
FIG. 3 is a time response plot for an excitation signal sent through three wires of the measurement tool of FIG. 2, each in open circuits, to determine marker location, in accordance with an embodiment.

FIG. 3 is a time response graph 150 for an excitation signal sent through three wires, each in open circuits, to determine marker location, in accordance with an embodiment. The horizontal axis 152 represents time in nanoseconds (ns) and the vertical axis 154 represents amplitude (e.g., in volts). As shown, between about 200 ns and 325 ns, the response signals for a first wire 156, a second wire 158, and a third wire 160 generally track one another. Around 325 ns, the response signal of the third wire 160 separates from the response signals of the first and second wires 156, 158, indicating a marker. That is, the time at which the response signal for the third wire 160 diverges from the response signals of the first and second wires 156, 158, in the instant embodiment about 320 ns, is indicative of the time for the emitted signal to propagate to the end of the third wire and back to the controller 106. Though determining the location of markers based on the response signal of a single wire would be difficult, comparing the response signals of multiple wires to one another makes determining marker locations relatively simple.

Figure 4:
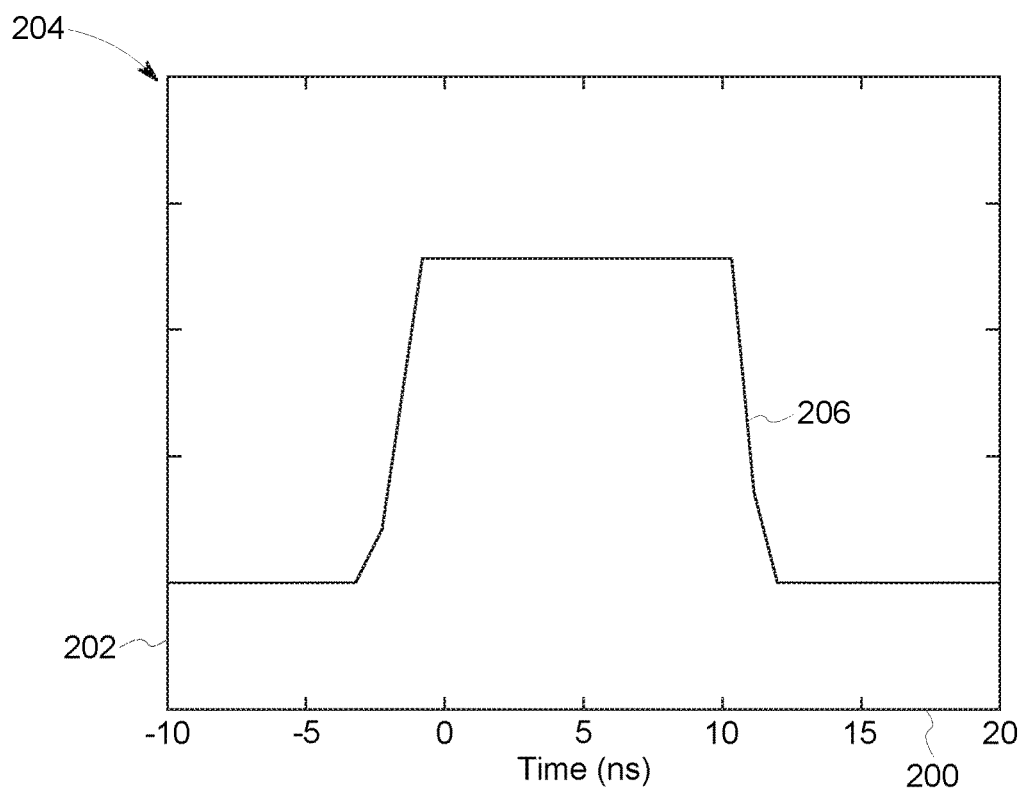
FIG. 4 is a plot of a sample input waveform for the time response measurement and analysis of FIG. 3, in accordance with an embodiment.

FIGS. 4-7 illustrate an input signal and time domain measurement and analysis of a test pipeline filled with three different fluids—air, water, and brine. For each graph, the horizontal axis 200 is representative of time (e.g., in ns), and the vertical axis 202 is representative of amplitude (e.g., voltage). FIG. 4 is a plot 204 of a sample input waveform 206 for time response measurement and analysis, in accordance with an embodiment. In the illustrated embodiment, the input waveform 206 is a simple square wave pulse lasting about 10 ns. However, as previously discussed, the input waveform 206 may be a simple pulse, or a more complex waveform that includes a range of frequencies (e.g., sinusoidal excitations or some other pattern generated using Fourier transforms). In the instant embodiment, the input waveform 206 is provided to two wires (e.g., one wire left open and one wire shorted against the wall of the pipeline) by the controller (e.g., via a bus) while the measurement device is in a pipeline filled entirely with air, water, and brine.

Figure 5:
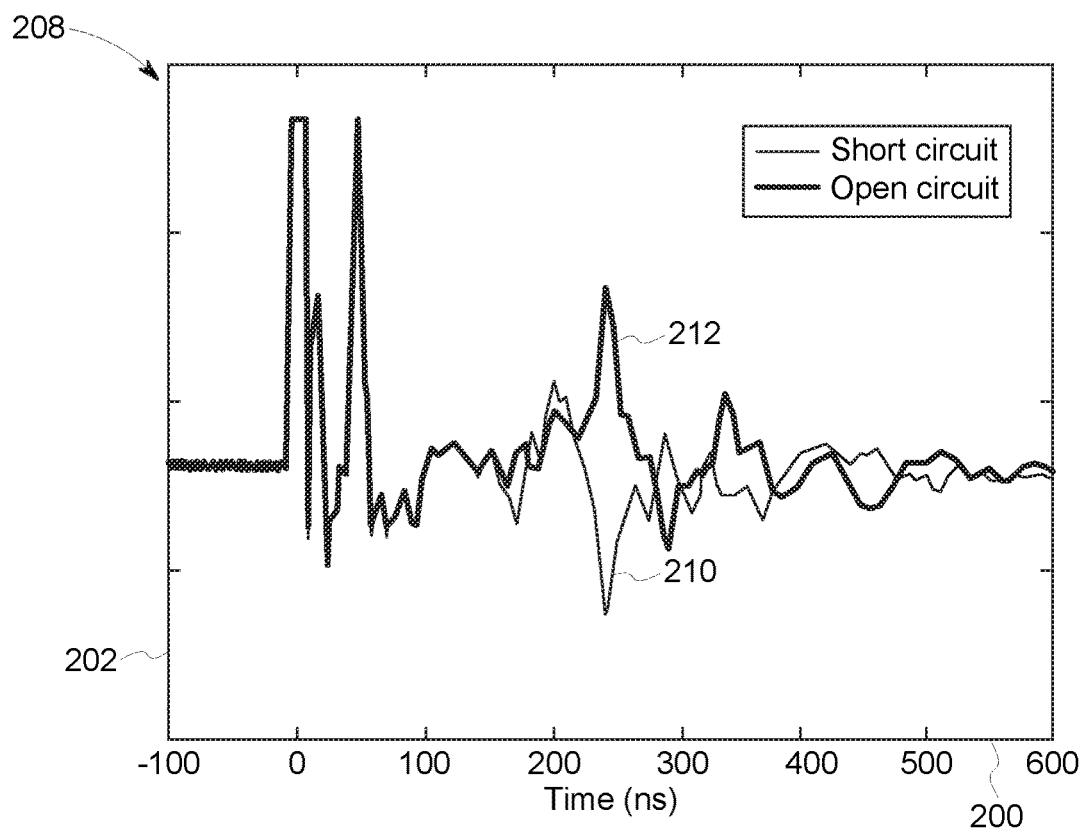
FIG. 5 is a plot of sample time domain responses to the input waveform of FIG. 4 for closed circuit and open circuit wires of the same length in a pipeline full of air, in accordance with an embodiment.

FIG. 5 is a plot 208 of sample time domain responses to the input waveform 206 of FIG. 4 for closed circuit 210 and open circuit 212 wires of the same length in a pipeline full of air, in accordance with an embodiment. As shown, the closed circuit and open circuit responses 210, 212 generally track one another until about 250 ns, at which point the two response signals diverge and become inverses of one another. The "delay" corresponds to the time at which the signals diverge from one another, which is indicative of time for the emitted signal to travel to the end of the wire and back. Accordingly, through air only, the delay for the experimental setup is determined to be about 250 ns.

Figure 6:
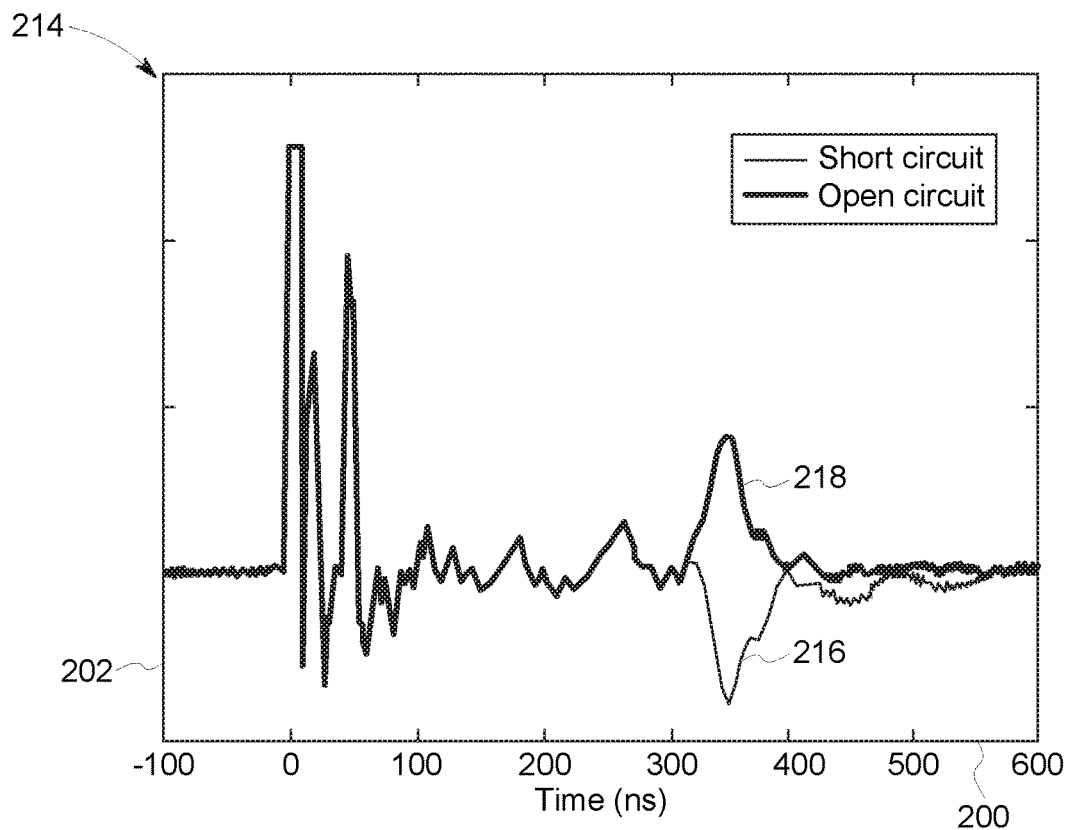
FIG. 6 is a plot of sample time domain responses to the input waveform of FIG. 4 for closed circuit and open circuit wires of the same length in a pipeline full of water, in accordance with an embodiment.

FIG. 6 is a plot 214 of sample time domain responses to the input waveform 206 of FIG. 4 for closed circuit 216 and open circuit 218 wires of the same length in a pipeline full of water, in accordance with an embodiment. As shown, the closed circuit and open circuit responses 216, 218 generally track one another until about 350 ns, at which point the two response signals diverge from one another before converging again. Accordingly, through water only, the delay for the experimental setup is determined to be about 350 ns.

Figure 7:
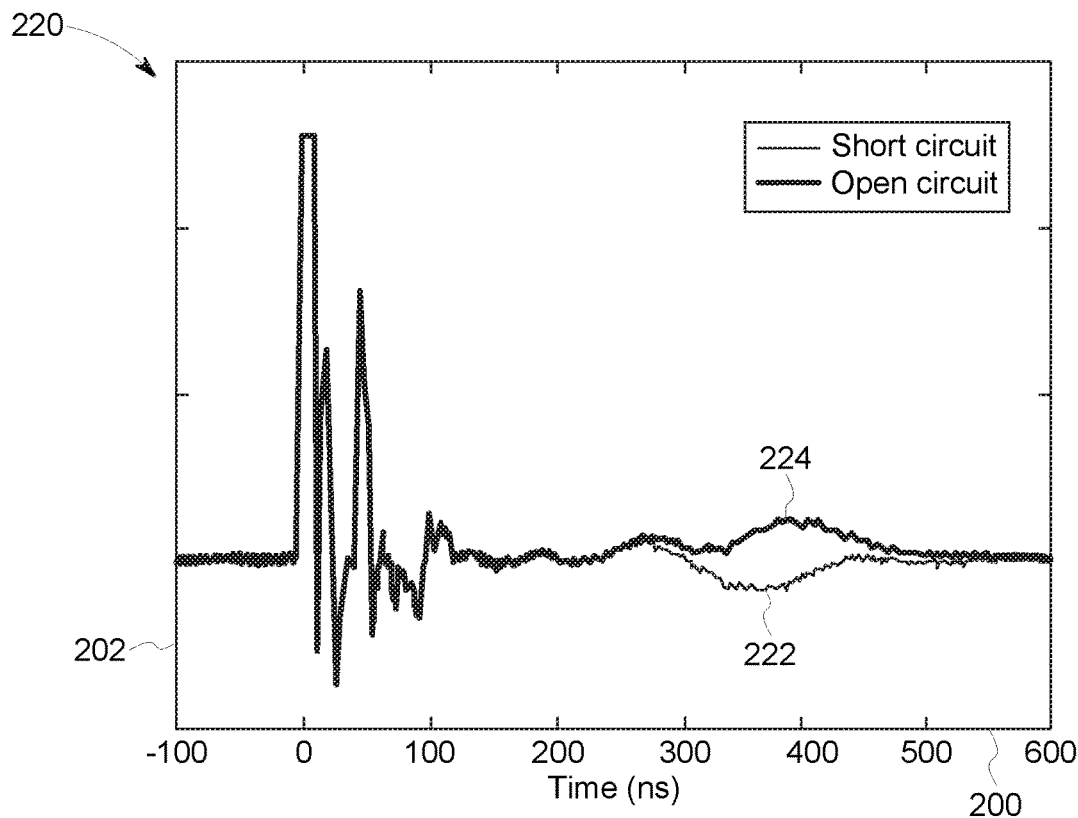
FIG. 7 is plot of sample time domain responses to the input waveform of FIG. 4 for closed circuit and open circuit wires of the same length in a pipeline full of brine, in accordance with an embodiment.

FIG. 7 is a plot 220 of sample time domain responses to the input waveform 206 of FIG. 4 for closed circuit 222 and open circuit 224 wires of the same length in a pipeline full of brine (e.g., salt water), in accordance with an embodiment. As shown, the closed circuit and open circuit responses 222, 224 generally track one another until about 350 ns, at which point the two response signals diverge from one another before converging again. Accordingly, through high conductivity brine only, the delay for the experimental setup is determined to be about 350 ns. Though the delays through water and brine are similar, the response signals in brine are attenuated (i.e., smaller magnitude amplitude) compared to the response signals in water.

Though each of the graphs 208, 214, 220 in FIGS. 5-7 illustrate signal response for a test pipeline filled with a single fluid (e.g., air, water, brine), these graphs show that the time delay for an emitted signal to propagate to the end of a wire and reflect back to a sensor can be determined, and that the time delay changes dependent upon the fluid flowing through the pipeline. Thus, if the lengths of the wires are known, and the dielectric constants of the various component fluids flowing through the pipeline are known, the dielectric constant of the composite fluid, and thus the makeup of the composite fluid may be determined or estimated.

Figure 8:
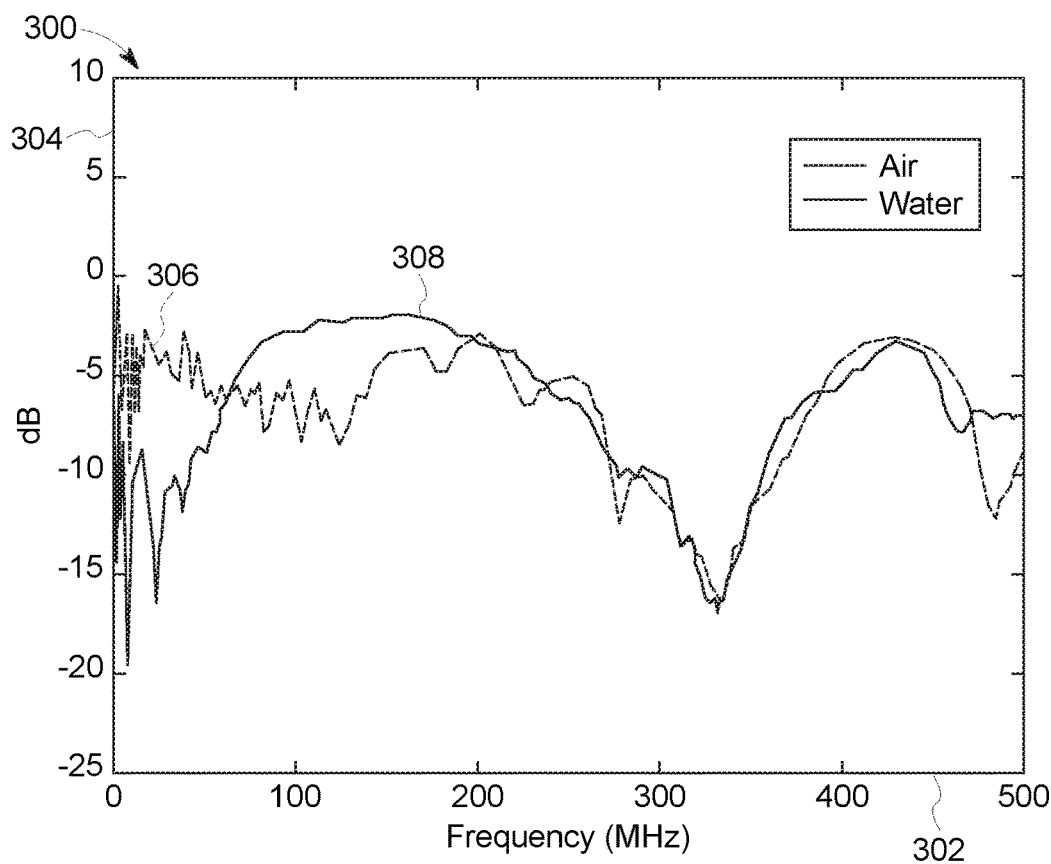
FIG. 8 is a plot of the broadband frequency domain response for pipelines filled with air and water, in accordance with an embodiment.
Figure 9:
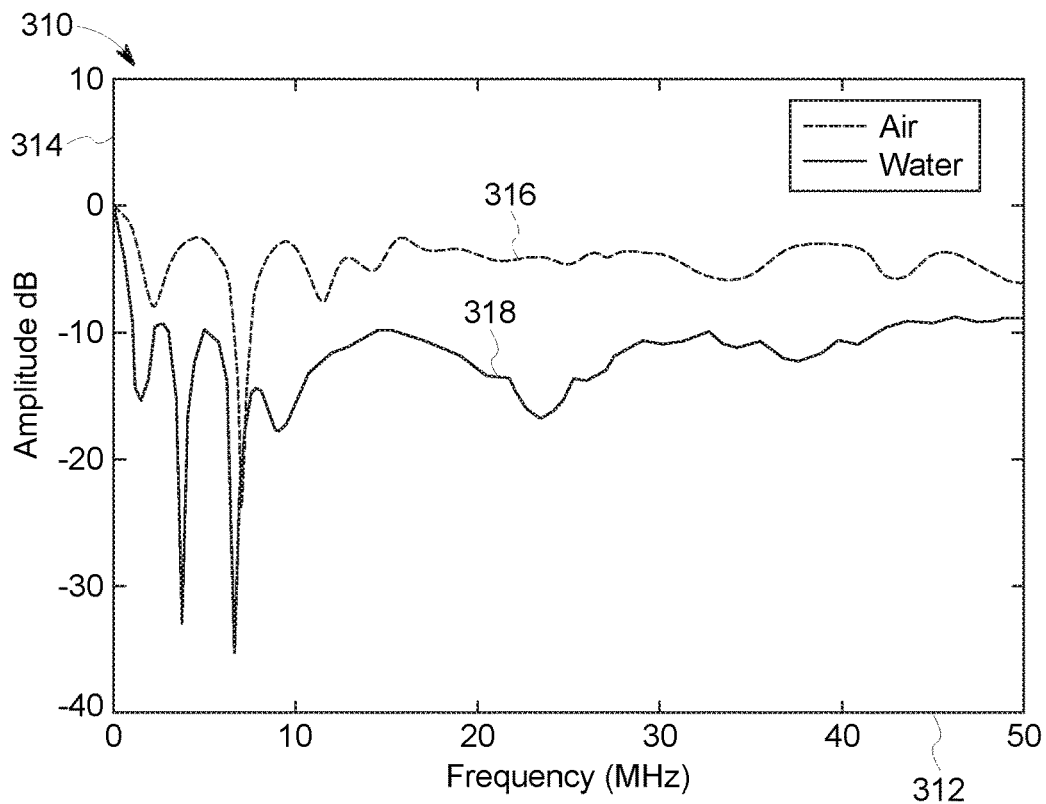
FIG. 9 is a plot of the amplitude frequency domain response for pipelines filled with air and water, in accordance with an embodiment.
Figure 10:
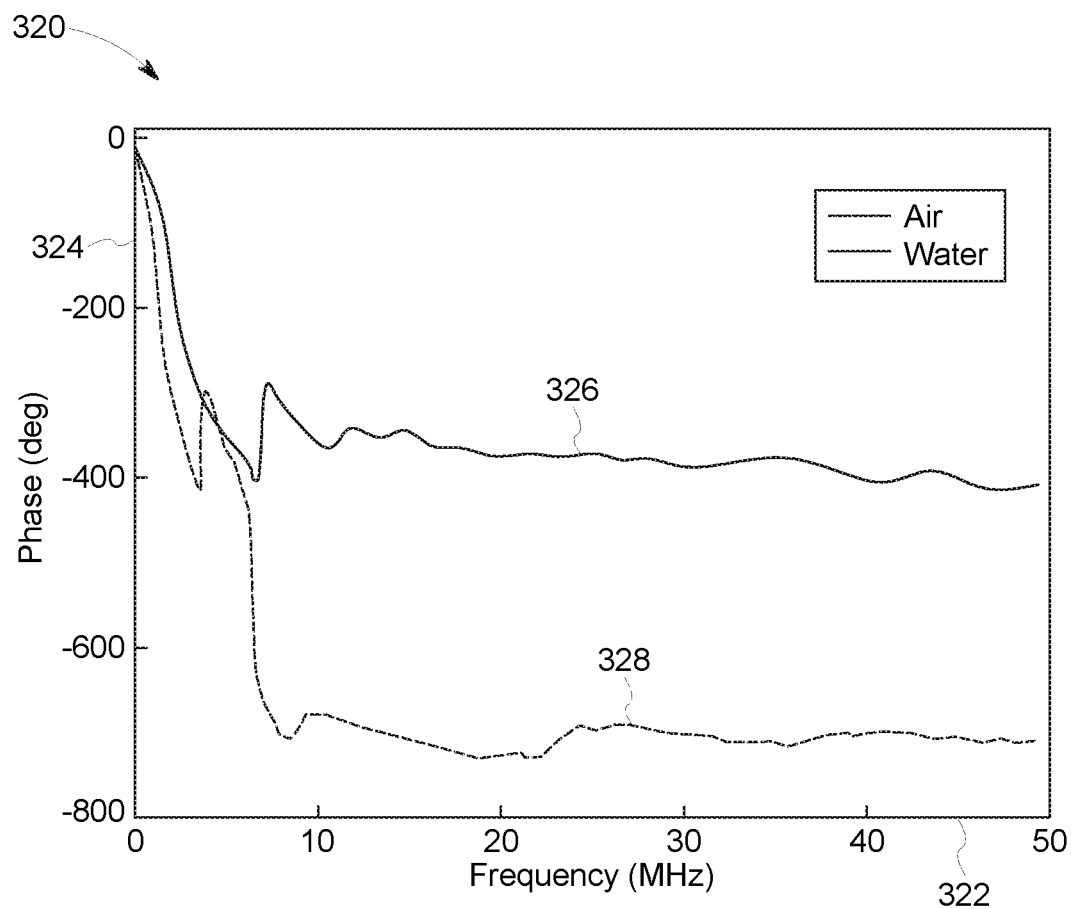
FIG. 10 is a plot of the phase angle frequency domain response for pipelines filled with air and water, in accordance with an embodiment.

In some embodiments, frequency domain measurement and analysis may be used in place of, or in addition to, time domain measurement and analysis. FIGS. 8-10 illustrate experimental frequency domain measurements taken with a one-port vector network analyzer (VNA). The VNA excites the wires at a series of frequencies and measures the amplitude. Rather than the several hundred nanoseconds that it takes for a time domain measurement, a frequency domain measurement may take several seconds. However, frequency domain measurement and analysis more broadly characterizes the system by probing a wide range of frequencies. FIG. 8 is a plot 300 of the broadband frequency domain responses for pipelines filled with air and water. The horizontal axis 302 represents frequency (e.g., in MHz) and the vertical axis 304 represents amplitude (e.g., in dB). One line 306 represents the frequency response in air, while the other line 308 represents the frequency response in water. As illustrated, below about 100 MHz, the response for the pipeline filled with air 306 has a higher amplitude than the frequency response of the pipeline filled with water 308. Between about 100 MHz and 200 MHz, the trend switches and the frequency response of the pipeline filled with water 308 has a higher amplitude than the response for the pipeline filled with air 306. At frequencies beyond about 200 MHz, the two frequency responses 306, 308 generally track one another.

FIG. 9 is a plot 310 of the amplitude frequency domain response for pipelines filled with air and water. The horizontal axis 312 represents frequency (e.g., in MHz) and the vertical axis 314 represents amplitude (e.g., in dB). One line 316 represents the frequency response in air, while the other line 318 represents the frequency response in water. As illustrated, the response for the pipeline filled with air 316 has a higher amplitude for almost all the sampled frequencies than the frequency response of the pipeline filled with water 318. Given that water is more conductive than air, it is to be expected that the frequency domain response in water is attenuated relative to the frequency domain response in air.

FIG. 10 is a plot 320 of the "unwrapped" phase (e.g., phase angle) frequency domain response for pipelines filled with air and water. The horizontal axis 322 represents frequency (e.g., in MHz) and the vertical axis 324 represents phase angle (e.g., in degrees). One line 326 represents the phase angle of the frequency response in air, while the other line 328 represents the phase angle of the frequency response in water. As illustrated, at frequencies less than about 5 MHz, the phase angle of the frequency response in both air 326 and water 328 are generally linear, but above about 5 MHz, the phases of the frequency response become non-linear. Linear frequency response is generally easier to analyze and draw conclusions from than non-linear frequency response. Accordingly, in the instant embodiment, focusing on lower frequencies may be beneficial. Further, the phase angle of the response for the pipeline filled with air 326 is steeper than the phase angle of the frequency response in water 328, indicating less delay (i.e., faster rate of propagation). Based on the frequency response shown in FIGS. 8-10, the dielectric constant of the fluid in the pipeline may be estimated. If the dielectric constants of the various component fluids of a composite fluid in the pipeline are known, then an estimate of the makeup of the composite fluid (e.g., by volume or by mass percentages of the various components) can be determined.

As previously discussed, measurement and analysis using the measurement tool may utilize time domain, frequency domain, or both in combination. FIGS. 11-13 illustrate experimental results, including time domain and frequency domain for a test pipeline filled with air and various ratios of crude oil. FIG. 11 is a plot 400 of a time domain response to an input waveform for a pipeline filled with air, a ¼ crude oil mixed fluid, a ½ crude oil mixed fluid, and a full crude oil fluid. The horizontal axis 402 corresponds to time (e.g., in ns) and the vertical axis corresponds to amplitude (e.g., voltage). Line 406 is the time domain response for the pipeline filled with air, line 408 is the time domain response for the pipeline filled with a ¼ crude oil mixed fluid, line 410 is the time domain response for the pipeline filled with a ½ crude oil mixed fluid, and line 412 is the time domain response for the pipeline filled with a full crude oil fluid. Though the response 410 for the pipeline filled with the ½ crude oil mixed fluid takes a slightly different shape than the frequency responses of the other fluids, the trend is clear. As the percentage of crude oil in the fluid in the pipeline increases, so does the delay in the signal propagating through the wires, as evidenced by the shift to the right of the responses 406, 408, 410, 412 as the percentage of crude oil in the fluid increases. Based on the delay, the dielectric constant of the composite fluid in the pipeline can be estimated. If the dielectric constant of each component fluid (e.g., crude oil and water) is known, the makeup of the composite fluid can be determined.

FIG. 12 is a plot 414 of a frequency domain amplitude response to an input waveform for the pipeline filled with air, the ¼ crude oil mixed fluid, the ½ crude oil mixed fluid, and the full crude oil fluid. The horizontal axis 416 corresponds to frequency (e.g., in MHz) and the vertical axis corresponds to amplitude (e.g., dB). Line 420 is the frequency domain amplitude response for the pipeline filled with air, line 422 is the frequency domain amplitude response for the pipeline filled with the ¼ crude oil mixed fluid, line 424 is the frequency domain amplitude response for the pipeline filled with the ½ crude oil mixed fluid, and line 426 is the frequency domain amplitude response for the pipeline filled with the full crude oil fluid. As the percentage of crude oil in the fluid in the pipeline increases, the frequency at which the peak amplitude occurs decreases and the magnitude of the peak amplitude decreases (i.e., the response becomes more attenuated). Accordingly, based on the frequency domain amplitude response the dielectric constant of the composite fluid in the pipeline may be determined. If the dielectric constant of each component fluid (e.g., crude oil and water) is known, the makeup of the composite fluid can be determined.

FIG. 13 is a plot 428 of a frequency domain phase angle response to an input waveform for the pipeline filled with air, the ¼ crude oil mixed fluid, the ½ crude oil mixed fluid, and the full crude oil fluid. The horizontal axis 430 corresponds to frequency (e.g., in MHz) and the vertical axis corresponds to phase angle (e.g., in degrees). Line 434 is the frequency domain amplitude response for the pipeline filled with air, line 436 is the frequency domain amplitude response for the pipeline filled with the ¼ crude oil mixed fluid, line 438 is the frequency domain amplitude response for the pipeline filled with the ½ crude oil mixed fluid, and line 440 is the frequency domain amplitude response for the pipeline filled with the full crude oil fluid. As the percentage of crude oil in the fluid in the pipeline increases, the frequency decreases, shifting the curves 434, 436, 438, 440 to the right. Based on the frequency domain phase angle response, the dielectric constant of the composite fluid in the pipeline may be determined. If the dielectric constant of each component fluid (e.g., crude oil and water) is known, the makeup of the composite fluid can be determined.

Figure 14:
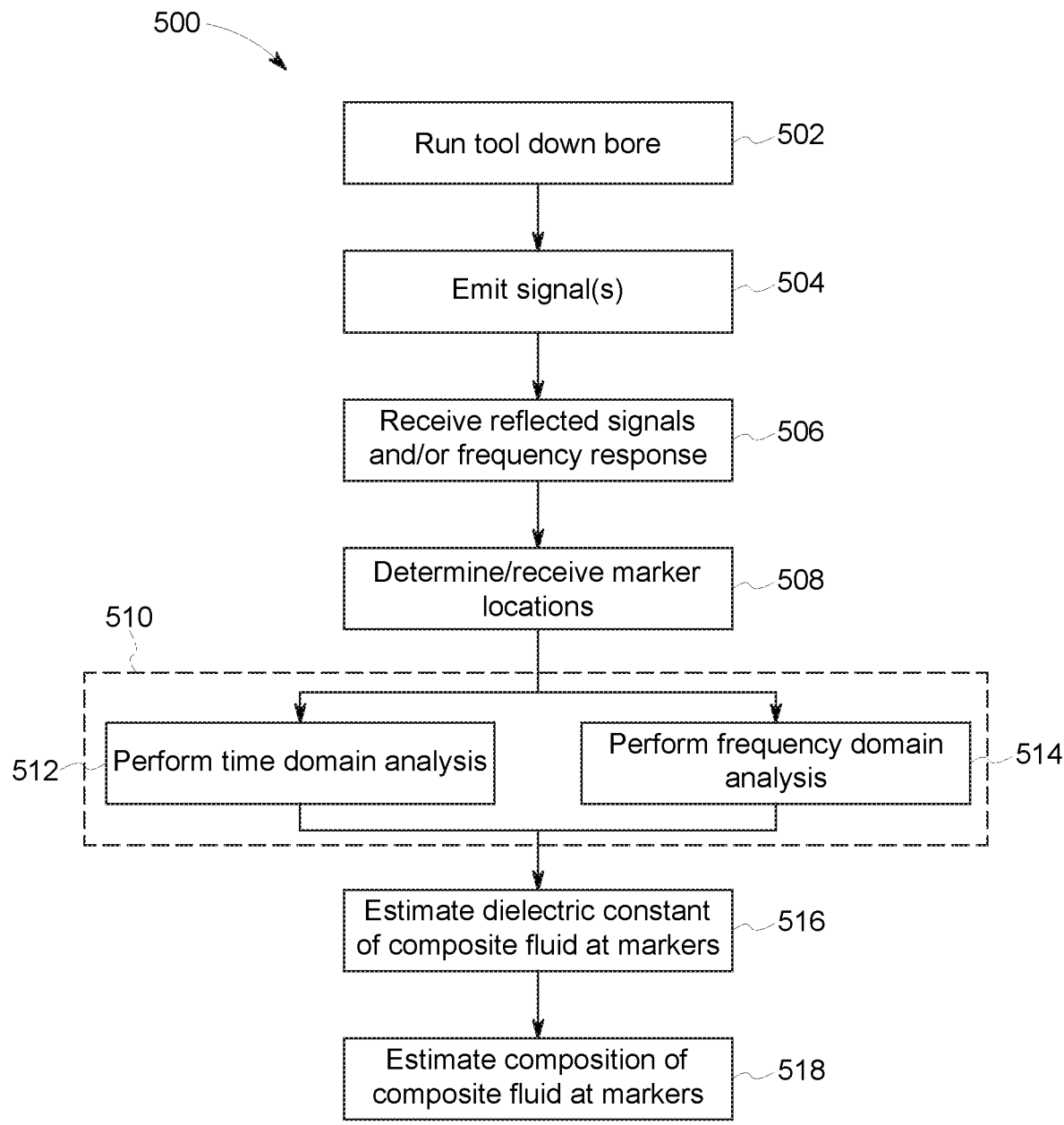
FIG. 14 is a flow chart of a process for determining the composition of a fluid flowing through a bore, at multiple locations, using the measurement tool shown in FIGS. 1 and 2, in accordance with an embodiment.

FIG. 14 is a flow chart of a process 500 for determining the composition of a fluid flowing through a bore, at multiple locations, using the measurement tool shown in FIGS. 1 and 2. At block 502, the measurement tool is run down the bore of the well to the desired location. The measurement tool may remain substantially stationary (e.g., along the axis of the bore) as it takes multiple measurements, or the measurement tool may move locations between measurements in order to take measurements from a variety of locations.

At block 504, the controller of the measurement tool emits one or more signals into the wires (e.g., via a bus) that are wrapped in a helical shape around the dielectric core. The wires may extend various lengths along the core in order to take measurements from various locations along the core. Further, the wires may be left open at the ends, or may be shorted against other wires or the pipeline wall. As previously discussed, the input waveform for the emitted signal or signals may be a simple square wave pulse, sinusoidal excitations, or some other pattern (e.g., generated using Fourier transforms) over a wide range of frequencies. The signals the propagate along the wires, reaching the ends of the wires and the propagating back toward the controller. At block 506, the controller (e.g., via the sensor) receives the reflected signals and/or the frequency response.

At block 508, the time delays to the marker locations are received or determined. In some embodiments, the marker locations may be determined ahead of time and provided to the user (e.g., by the manufacturer of the measurement tool). In other embodiments, the marker locations may be determined based on the collected data by comparing received signals from multiple wires of different lengths.

At block 510, the data is analyzed to determine the delay in the signal propagating down the wire and returning to the controller. As previously discussed, data analysis may include time domain analysis (block 512), frequency domain analysis (block 514), or both. At block 516, the dielectric constant of the composite fluid at each marker is estimated based on the data analysis performed in block 510. At block 518, the composition of the composite fluid at each marker location is estimated based on the known dielectric constant of each component fluid. Wells typically include multiple injection points at which chemicals may be injected to improve flow of hydrocarbons through the bore. By using the measurement tool to determine the fluid composition at or near one or more of the injection points, an operator can make determinations regarding what chemicals should be injected through which injection points, and how much of the selected chemicals should be injected, to improve the flow of hydrocarbons produced by the well.

The disclosed techniques include systems and methods for determining the composition of fluid flowing through a bore at multiple locations. Specifically, one or more wires are wrapped around a dielectric core in a helical shape. The one or more wires may be of different lengths, extending to various locations along the measurement tool. Excitation signals (e.g., single pulses or more complex input waveforms spanning a range of frequencies) are emitted to the wires and propagate down the lengths of the wires, reaching the ends of the wires, and then propagating back along the wires. The reflected waves or frequency responses are received and analyzed to determine a delay in each signal propagating down the wires. Based on the analysis, the dielectric constant of the fluid flowing through the bore may be determined at each of the locations. If the dielectric constants of each component fluid (e.g., water, crude oil, etc.) is known, then the composition of the fluid may be determined. Using this information, decisions regarding what chemicals to inject, where, and how much may be made to improve the production of hydrocarbons by the well and mitigate obstructions.

This written description uses examples to disclose the claimed subject matter, including the best mode, and also to enable any person skilled in the art to practice the disclosed subject matter, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A measurement tool configured to be run through a bore of a hydrocarbon well, the measurement tool comprising:
   a dielectric core;
   a controller disposed at a first end of the dielectric core;
   a first wire helically disposed about the dielectric core and exposed to the bore of the hydrocarbon well, wherein the first wire extends from the controller to a first location a first distance from the controller; and
   a second wire helically disposed about the dielectric core and exposed to the bore of the hydrocarbon well, wherein the second wire extends from the controller to a second location a second distance from the controller;
   wherein the controller is configured to provide first and second input signals to the first and second wires, and receive first and second reflected signals from the first and second wires, and
   wherein the first wire is in contact with a pipeline wall that defines the bore.

2. The measurement tool of claim 1, wherein the first distance is greater than the second distance.

3. The measurement tool of claim 1, wherein the first wire is in contact with the second wire.

4. The measurement tool of claim 1, comprising a mechanism configured to open and close a circuit between the first wire and a pipeline wall that defines the bore.

5. The measurement tool of claim 4, wherein the mechanism comprises a servo, a linear motor, a switch, or a combination thereof.

6. The measurement tool of claim 1, wherein the first input signal comprises a pulse.

7. The measurement tool of claim 1, wherein the first input signal comprises a frequency domain excitation signal spanning a range of frequencies.

8. A system, comprising:
a measurement tool configured to be run through a bore of a hydrocarbon well the measurement tool comprising:
a dielectric core;
a controller disposed at a first end of the dielectric core;
a first wire helically disposed about the dielectric core and exposed to the bore of the hydrocarbon well, wherein the first wire extends from the controller to a first location a first distance from the controller, and wherein the first wire is in contact with a pipeline wall that defines the bore; and
a second wire helically disposed about the dielectric core and exposed to the bore of the hydrocarbon well, wherein the second wire extends from the controller to a second location a second distance from the controller;
wherein the controller is configured to provide first and second input signals to the first and second wires, and receive first and second reflected signals from the first and second wires; and
a computing device configured to analyze the received first and second reflected signals to determine a first dielectric constant of a fluid in the bore at the first location, and a second dielectric constant of the fluid in the bore at the second location.

9. The system of claim 8, wherein the computing device is configured to determine a first composition of the fluid in the bore at the first location, and a second composition of the fluid in the bore at the second location.

10. The system of claim 8, wherein the first input signal comprises a pulse.

11. The system of claim 8, wherein the first input signal comprises a frequency domain excitation signal spanning a range of frequencies.

12. The system of claim 8, wherein analyzing the received first and second reflected signals comprises determining a delay in signal propagation through the first and second wires.

13. The system of claim 8, wherein analyzing the received first and second reflected signals comprises a time domain analysis.

14. The system of claim 8, wherein analyzing the received first and second reflected signals comprises a frequency domain analysis.

15. A method, comprising
running a measurement tool down a bore of a hydrocarbon well wherein, the measurement tool comprises a first wire disposed about a dielectric core and extending from a controller to a first location a first distance from the controller, and a second wire disposed about the dielectric core and extending from the controller to a second location a second distance from the controller, wherein the first wire and the second wire are disposed about the dielectric core in a helical shape and exposed to the bore of the hydrocarbon well, and
wherein the first wire is in contact with a pipeline wall that defines the bore;
providing, via the controller, first and second input signals to the first and second wires; and
receiving, via the controller, first and second reflected signals from the first and second wires.

16. The method of claim 15, comprising analyzing the received first and second reflected signals to determine a first dielectric constant of a fluid in the bore at the first location, and a second dielectric constant of the fluid in the bore at the second location.

17. The method of claim 16, comprising determining a first composition of the fluid in the bore at the first location, and a second composition of the fluid in the bore at the second location.

18. The method of claim 16, wherein analyzing the received first and second reflected signals comprises performing a time domain analysis.

19. The method of claim 16, wherein analyzing the received first and second reflected signals comprises performing a frequency domain analysis.

* * * * *